US00PP11539P

United States Patent [19]

Olesen et al.

[11] Patent Number: Plant 11,539

[45] Date of Patent: Oct. 3, 2000

[54] MINIATURE ROSE PLANT NAMED 'POULPOLLO'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/113,907

[22] Filed: Jul. 10, 1998

[51] Int. Cl.[7] ..... A01H 5/00

[52] U.S. Cl. ..... Plt./116

[58] Field of Search ..... Plt./116, 119, 121

*Primary Examiner*—Howard J. Locker

[57] ABSTRACT

A new miniature rose plant which has abundant bronze-peach blend flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE DISCOVERY

The present discovery constitutes a new and distinct variety of miniature rose plant which was discovered in a cultivated area. The mutation resulted from 'POULprima', a patented variety hybridized by the same inventors, described and illustrated in U.S. Plant Pat. No. 9,482 and issued on Mar. 26, 1996. The new rose variety resulted from a naturally occurring mutation of unknown causation on a branch of 'POULprima' which was discovered in a controlled planting. The new variety is named 'POULpollo'.

The rose plant of the present discovery has a unique combination of characteristics which are outstanding in the new variety and which distinguish it from the original rose 'POULprima' as well as all other varieties which we are aware of. For example, the new variety has:

1. Abundant bronze-peach flowers;
2. Vigorous and compact growth;
3. Year-round flowering under glasshouse conditions;
4. Suitability for production from softwood cuttings in pots;
5. Durable flowers and foliage which make the variety suitable for distribution in the floral industry.

This combination of qualities is not present in previously available commercial cultivars of this type and distinguish 'POULpollo' from all other varieties of which we are aware.

The resulting mutation was evaluated and trials were conducted of the resulting rose plants in a controlled environment.

Asexual reproduction of 'POULpollo' by cuttings was first done by L. Pernille and Mogens N. Olesen in their nursery in Fredensborg, Denmark in April, 1995. This initial and other subsequent propagations have demonstrated that the characteristics of 'POULpollo' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULpollo'. Specifically illustrated in SHEET 1:

1. Stem or entire plant showing branching and the attachment of leaves, buds, and peduncles;
2. Flower bud, partially opened bud, and open bloom;
3. Flower petals, detached;

4. Sepals, receptacle, and pedicel;
5. Flowering stem as well as a bare stem exhibiting thorns;
6. Leaves.

DETAILED DESCRIPTION OF THE VARIETY

The following is a detailed description of 'POULpollo', as observed in its growth in glasshouses in Fredensborg, Denmark and Half Moon Bay, Calif. and in field nursery in Jackson County, Oreg. Color references are made using The Royal Horticultural Society (London, England) Colour Chart, 1995, except where common terms of color are used.

For a comparison, the nearest existing rose variety is 'POULprima', a patented variety described and illustrated in U.S. Plant Pat. No. 9,482 and issued on Mar. 26, 1996. Chart 1 details several physical characteristics of POULpollo and POULprima.

CHART 1

| | 'POULpollo' | 'POULprima' |
|---|---|---|
| Bud color at ¼ open | Blend of Orange Group 29B and 24C | Red-Purple Group 61C |
| Upon opening, Color of Upper surface of Petal | Orange Group 27A | Red-Purple Group 61C |
| Open flower, Color of upper surface of petal, outermost petals | Red Group 36C | Red-Purple Group 61C |
| Open flower, Color of upper surface of petal, innermost petals | Orange Group 24C | Red-Purple Group 61C |
| Basal petal spot | Outer petals: Yellow Group 12B Inner petals: Yellow Group 12B | Outer petals: Yellow Group 4C Inner petals: Yellow Group 4A |

Parentage: Mutation of 'POULprima'.

Classification:

*Botanical.*—*Rosa hybrida.*

*Commercial.*—Miniature.

FLOWER AND FLOWER BUD

Blooming habit: Continuous.

Flower bud:

*Size.*—Upon opening, 16 mm–18 mm in length.

*Bud form.*—Pointed to pointed ovoid.

*Bud color.*—Blend of Orange Group 29B and 24C at ¼ opening. At ¼ opening the upper petal surface is a blend of Orange Group 29B and 24C and the reverse surface is a blend of Orange Group 28B and 28C.

*Sepals.*—Green Group 138A. Weak foliaceous appendages on three of the five sepals. Surfaces of sepals moderately pubescent. Stipitate glands on sepals with appendages.

*Peduncle.*—Surface: Smooth. Length: 15 mm–18 mm average length. Color: Green Group 143B. Prickles: None. Stipitate glands present. Strength: Upright, stiff.

*Receptacle.*—Surface: Smooth. Shape: Urn-shaped. Size: Medium. 5 mm×6 mm. Color: Green Group 143B.

*Borne.*—Multiple buds per stem. 2–5 buds per flowering shoot.

Flower bloom:

*Size.*—Medium for 10 cm pot rose. 40–45 mm. on average.

*Form.*—Upon opening: form of upper part of flower is flat. Completely open: upper part of flower is flat. Lower part of flower is a flattened convex. Outermost petals double reflexed.

*Petalage.*—Double. Average range: 30–35 under normal conditions.

*Color.*—Upon opening, upper surface of marginal zone and middle zone of petal is Orange Group 27A. Upon opening, reverse surface of marginal zone and middle zone of the petal is a blend of Red Group 48D and Orange Group 29C. After opening, the upper surface of the outermost petals is Red Group 36C. After opening, the upper surface of the innermost petals is Orange Group 24C. After opening, the color of the reverse surface of the marginal and middle zone of the innermost petals is between Greyed-Red Group 179C and 179D. After opening, the color of the reverse surface of the marginal and middle zone of the outermost petals is between Red Group 50C and 50D.

*General tonality.*—Blend of Greyed-Orange Group 170C and Orange Group 28D–29D. A small petal spot Yellow Group 12B exists on the inner side of the petal base. A small petal spot Yellow Group 12B exists on the outer side of the petal base.

*Other.*—Mid-rib of petal on reverse surface is Yellow Group 12C.

*Petal reflex.*—Innermost petals reflexed slightly. Outermost petals double reflexed.

*Petaloids.*—Present. 5–10 per bloom.

*Fragrance.*—Light. Lightly fruity.

*Duration.*—As a pot plant, flowers last from 15 to 18 days. As a cut flower 10 to 12 days.

Reproductive organs:

*Pollen.*—Color: Yellow-Orange Group 15B. Abundance: Abundant.

*Anthers.*—Size: Medium. Color: Yellow-Orange Group 15B. Abundance: Above average.

*Filaments.*—Color: Yellow-Green Group 154B.

*Stigmas.*—Superior in location to anthers. Color: Yellow-Green Group 150C.

*Styles.*—Color: Yellow-Green Group 150C.

PLANT

Plant growth: Vigorous, compact, upright to bushy. When grown as a 10 cm pot plant, the average height of the plant itself is 16–18 cm and the average width is 16–18 cm. When grown as a nursery plant on its own roots the average plant height is 25–35 cm and the average plant width is 20–25 cm.

Stems:

*Color.*—Young wood: Green Group 138A. Older wood: Green Group 138A.

*Thorns.*—Incidence: Few thorns. Size: Average length 3 mm. Color: Green-White Group 157A. Shape: Linear.

*Bark.*—Young wood: Smooth. Older wood: Smooth.

Plant foliage: Normal number of leaflets on normal leaves in middle of the stem: 5 leaflets.

*Leaf size.*—Medium. 80 mm×60 mm.

*Quantity.*—Abundant.

*Color.*—Upper Leaf Surface: Dark green. Between Green Group 137A to 139A. Lower Leaf Surface: Medium green. Green Group 138B. Juvenile foliage: Green Group 138B. Underside of leaves with red intonations of Greyed-Red Group 179B.

Plant leaves and leaflets:

*Stipules.*—Small. Size: 5 mm–7 mm. Hairs: Limited hairs on margin. Color: Green Group 137C.

*Petiole.*—Length: 15–20 mm. Underneath: With several small prickles. Color: Green Group 137C.

*Rachis.*—Green Group 137C with several small prickles.

*Leaflet edge.*—Finely serrated.

*Shape.*—Leaflets are pointed ovate.

*Leaflets.*—Number: Generally 5.

*Other.*—Matte finish with slight gloss. Thick texture. Leathery.

Disease resistance: Above average resistance to mildew and Botrytis under normal growing conditions in Half Moon Bay, Calif. and Fredensborg, Denmark.

We claim:

1. A new and distinct variety of rose plant of the miniature class, substantially as herein illustrated and described as a distinct and novel rose variety due to its abundant bronze-peach blend flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

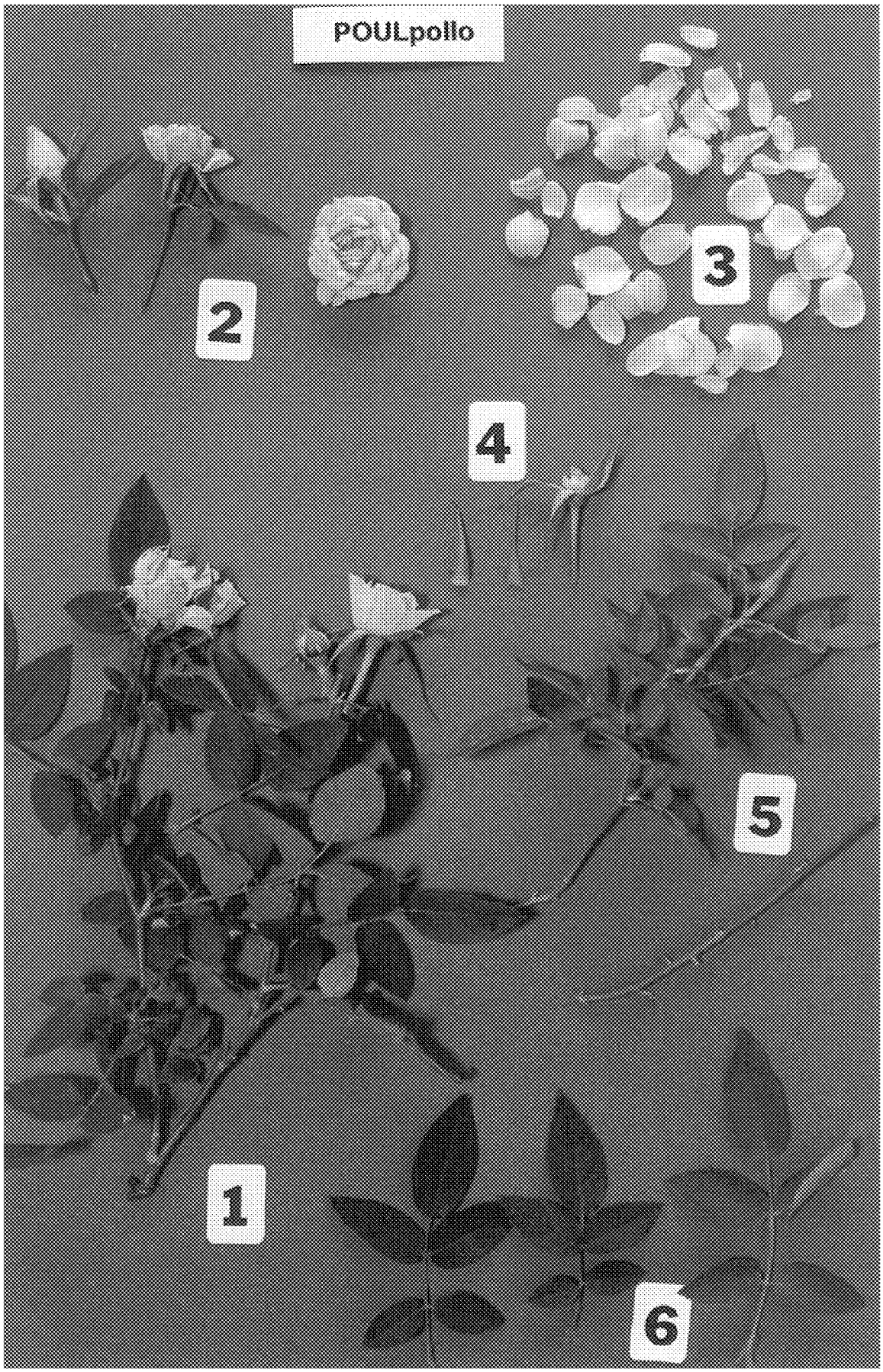
POULpollo
2
3
4
5
1
6